United States Patent
Zitelli et al.

(10) Patent No.: US 11,419,725 B2
(45) Date of Patent: Aug. 23, 2022

(54) IMPLANTS INCLUDING A MONOLITHIC LAYER OF BIOCOMPATIBLE METALLIC MATERIAL

(71) Applicant: Zimmer, Inc., Warsaw, IN (US)

(72) Inventors: Joseph Peter Zitelli, River Edge, NJ (US); Robert Joseph Gill, Florence, NJ (US); Steven Seelman, Montclair, NJ (US)

(73) Assignee: Zimmer, Inc., Warsaw, IN (US)

(*) Notice: Subject to any disclaimer, the term of this patent is extended or adjusted under 35 U.S.C. 154(b) by 162 days.

(21) Appl. No.: 16/194,729

(22) Filed: Nov. 19, 2018

(65) Prior Publication Data

US 2019/0151096 A1     May 23, 2019

Related U.S. Application Data (60) Provisional application No. 62/589,922, filed on Nov. 22, 2017.

(51) Int. Cl.
| | |
|---|---|
| *A61F 2/28* | (2006.01) |
| *A61L 27/56* | (2006.01) |
| *A61L 27/30* | (2006.01) |
| *A61L 27/08* | (2006.01) |
| *A61F 2/30* | (2006.01) |

(52) U.S. Cl.
CPC ............... *A61F 2/28* (2013.01); *A61L 27/08* (2013.01); *A61L 27/306* (2013.01); *A61L 27/56* (2013.01); *A61F 2/3094* (2013.01); *A61F 2002/30032* (2013.01); *A61F 2002/3092* (2013.01); *A61L 2430/02* (2013.01); *A61L 2430/20* (2013.01)

(58) Field of Classification Search
CPC ............ A61F 2/28; A61F 2/3094; A61F 2002/30032; A61F 2002/3092; A61F 2/24; A61F 2002/30003; A61F 2002/30028; A61L 27/56

See application file for complete search history.

(56) References Cited

U.S. PATENT DOCUMENTS

| | | | | |
|---|---|---|---|---|
| 2,766,112 | A | 10/1956 | Harald | |
| 5,282,861 | A * | 2/1994 | Kaplan | A61L 27/306 623/23.51 |
| 6,974,625 | B2 * | 12/2005 | Hunter | B32B 15/04 428/314.2 |
| 7,648,735 | B2 * | 1/2010 | Hunter | C23C 4/00 623/20.14 |
| 8,992,825 | B2 * | 3/2015 | Li | A61F 2/28 419/2 |
| 9,017,598 | B2 * | 4/2015 | Menchhofer | B22F 3/14 419/11 |

(Continued)

OTHER PUBLICATIONS

Levy, Roland A., "Investigation of Chemically Vapor Deposited Tantalum for Medium Caliber Gun Barrel Protection", SERDP Project WP-1425, New Jersey Institute of Technology, (Oct. 2008), 43 pgs.

*Primary Examiner* — Alvin J Stewart
(74) *Attorney, Agent, or Firm* — Schwegman Lundberg & Woessner, P.A.

(57) ABSTRACT

Various embodiments disclosed relate to an implant. The implant includes a substrate. The implant further includes a monolithic layer comprising a biocompatible metallic material, having at least one of an amorphous and a crystalline microstructure contacting the substrate.

20 Claims, 4 Drawing Sheets

(56) References Cited

U.S. PATENT DOCUMENTS

| | | |
|---|---|---|
| 9,277,998 B2 | 3/2016 | Vargas et al. |
| 9,981,063 B2 * | 5/2018 | O'Driscoll ............ A61L 27/3654 |
| 10,039,619 B2 * | 8/2018 | Vargas .................... A61K 6/802 |
| 2002/0169066 A1 * | 11/2002 | Cassidy .................... B28B 19/00 |
| | | 501/80 |
| 2005/0129949 A1 * | 6/2005 | Hunter ...................... A61L 27/56 |
| | | 428/408 |
| 2005/0131521 A1 * | 6/2005 | Marton ...................... A61L 31/12 |
| | | 623/1.13 |
| 2005/0246032 A1 * | 11/2005 | Bokros .............. A61M 39/0247 |
| | | 623/901 |
| 2006/0020346 A1 * | 1/2006 | Hunter ...................... B32B 15/04 |
| | | 623/23.51 |
| 2008/0064101 A1 * | 3/2008 | Pykett .................... C12N 5/0636 |
| | | 435/373 |
| 2012/0321779 A1 | 12/2012 | Vargas et al. |
| 2013/0131699 A1 * | 5/2013 | Jiang ...................... A61F 2/0811 |
| | | 606/151 |
| 2013/0325142 A1 | 12/2013 | Hunter et al. |
| 2014/0088716 A1 | 3/2014 | Zubok et al. |
| 2018/0200409 A1 * | 7/2018 | Largeteau ................ C04B 30/00 |
| 2019/0099273 A1 * | 4/2019 | Servidio ............. A61F 2/30749 |
| 2019/0151096 A1 * | 5/2019 | Zitelli ...................... A61L 27/08 |

\* cited by examiner

IMPLANTS INCLUDING A MONOLITHIC LAYER OF BIOCOMPATIBLE METALLIC MATERIAL

CLAIM OF PRIORITY

This application claims the benefit of U.S. Provisional Patent Application Ser. No. 62/589,922, filed on Nov. 22, 2017, the benefit of priority of which is claimed hereby, and which is incorporated by reference herein in its entirety.

BACKGROUND

Implantable devices can replace or augment body components or portions of body components that cannot be regenerated or are no longer functioning properly. Examples of implantable devices include heart valves, pacemakers, spinal implants, dental implants, breast implants, collagen for soft tissue augmentation, and orthopedic devices, such as artificial knee, hip, and ankle joints.

Some implantable devices can include a porous scaffold material, such as to provide structural support to an orthopedic implant, to fill a void in bone reconstruction or joint repair, or to provide a structure for permitting ingrowth and attachment of tissue. Porous scaffolds can be used to provide structural support to a patient's tissue, such as bone tissue. Porous scaffolds can also be used to provide an attachment structure for coupling or attachment of a patient's tissue, such as via ingrowth and bonding between the patient's tissue and the porous scaffold.

SUMMARY OF THE DISCLOSURE

The present disclosure provides an implant. The implant includes a substrate. The implant further includes a monolithic layer comprising a biocompatible metallic material, having at least one of an amorphous and a crystalline microstructure contacting the substrate.

The present disclosure further provides a method of making an implant. The implant includes a substrate. The implant further includes a monolithic layer comprising a biocompatible metallic material, having at least one of an amorphous and a crystalline microstructure contacting the substrate. The method includes contacting the substrate with a monolithic layer precursor. The method further includes reducing most of the monolithic layer precursor (e.g., about 90 percent to 100 percent) on the substrate to form the monolithic layer of the biocompatible material.

The implantable device of the present disclosure provides various advantages and benefits, some of which are unexpected. For example, according to some embodiments, the implantable material can be manufactured faster than a corresponding (e.g., identical constituents) implantable material that relies exclusively on chemical-vapor-deposition to build a layer of biocompatible metallic material. According to some embodiments, the layer of biocompatible metallic material can be a monolithic layer, which can provide increased strength relative to a corresponding layer of the biocompatible metallic material formed exclusively by chemical-vapor-deposition. According to some embodiments, the layer of biocompatible metallic material can be distributed more uniformly (e.g., constant thickness or complete coverage of a substrate) than a corresponding layer of the biocompatible metallic material formed exclusively by chemical-vapor-deposition.

BRIEF DESCRIPTION OF THE FIGURES

The drawings illustrate generally, by way of example, but not by way of limitation, various embodiments discussed in the present document.

DETAILED DESCRIPTION OF THE DISCLOSURE

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

Cancellous, or spongy, bone is composed of a porous space-frame structure formed of open spaces defined by interconnected trabeculae, oriented along lines of principal stresses. At the microstructural level, the trabeculae are composed of layers of lamellar bone. Cancellous bone has anisotropic mechanical properties, for example, different structural behavior along different orientations. Along the axis of the major channels, cancellous bone exhibits elastic behavior with sudden brittle failure at ultimate load in tension. When loaded with a tensile force whose line of action is skewed with respect to the channel axis of the bone, the stress-strain curve is parabolic with plastic deformation and greater energy absorption. It is therefore stiffer (has higher tensile and compressive moduli) but fails at a lower strain when loaded parallel to the predominant spicular direction than when loaded in other directions. These properties are important because they serve to absorb shock and distribute load in the vicinity of the articular surfaces of joints.

Any implantable material to be used as a substitute for cancellous bone should allow elastic deformation and load distribution. In addition, the material should not produce load concentrations, particularly if placed close to the underlying surface of articular cartilage, which might increase the local stresses on the articular surface and lead to wear and damage of the surface.

Cancellous bone demonstrates remodeling behavior according to Wolff's Law: that is, with the form being given, bone adapts to the loads applied to it. The converse is also true, and equally important: where loads are not applied, bone tends to resorb. An implantable material should, therefore, distribute stresses throughout its structure, the ingrowing bone, and the surrounding bone in order to avoid bone resorption and weakening caused by stress shielding.

The density of cancellous bone is 0.7 g/cm$^3$; its tensile modulus 0.2-0.5 GPa; tensile strength 10-12 MPa; and strain to failure 5-7%. Compared to cortical bone, cancellous bone is ⅓-¼ as dense (indicating its porous nature); ¹⁄₁₀-¹⁄₂₀ as stiff; and five times as ductile. The mechanical properties of the two types, though, actually represent a continuum, reflecting the behavior of a relatively uniform material (bone) modified by differences in density and structure.

Based on experiments with hydroxyapatite implants, ingrowth and maturation of new bone are more rapid between a cancellous bone region than between cortical bone, with the tissue-implant interface reaching peak shear strength in dogs in 8 weeks. The process may take longer in humans, with remodeling still possible up to 2 years post-operation. Inadequate device designs may produce continued stress shielding remodeling as long as 9-10 years post-operation.

Materials for osseous, or bone, implants must be rigid and stress-resistant, while avoiding self-concentration of stresses that result in stress shielding. Also, osseous implants should ideally reside in the bone without interfering with bone remineralization, the natural process by which the body replenishes bone. The implant should be able to be precisely shaped and placed for optimal interface and performance. Finally, non-resorption would be a beneficial quality for implants used in load-bearing applications, and/or those in which complete bone ingrowth is not possible.

One factor relevant to the performance of an implantable material is the completeness of interconnectivity between the material and the bone. Constrictions between pores and isolated, dead-end pockets in the implantable material can limit vascular support to ingrowing tissues; ischemia of the ingrowing bone cells can result in failure of the implant. Incomplete vascularization or a reduction in the neovascularity can also make the implantable material vulnerable to bacterial colonization. Implantable materials lacking completely interconnected porosity can also result in aberrant mineralization, stress shielding, low fatigue strength, and/or bulk displacement.

Figure 1:
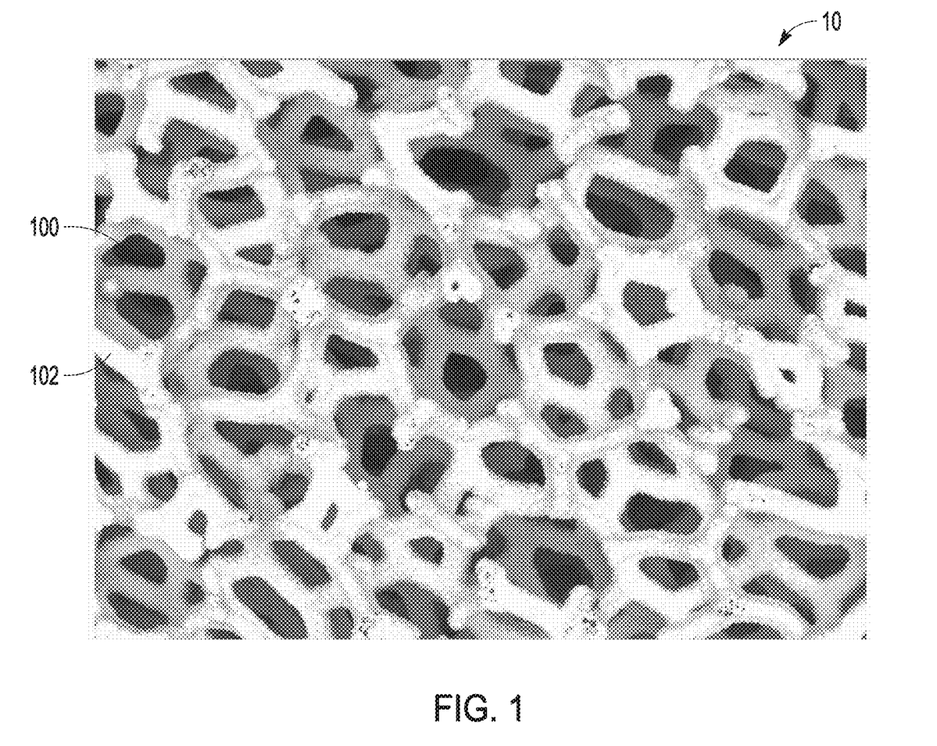
FIG. 1 is a scanning electron microscope image of a portion of an implantable material, according to various embodiments.

According to various embodiments, the implantable material of implant 10 shown in FIG. 1 provides an open cell metal structure including highly interconnected, three-dimensional porosity that is uniform and consistent, the structure is similar to that of natural cancellous bone. In this way it is superior to other porous metallic implant materials, whose "porosity" is artificially produced via some form of surface treatment that does not result in a truly complete, open porosity. Examples of these methods include macroscopic porous coatings (e.g. metal microspheres or wires sintered or otherwise attached to a bulk surface); microscopic surface porosity (e.g. metal powder particles flame- or plasma-sprayed onto a bulk surface); and controlled surface undulations machined into a bulk surface.

Although certain porous ceramic materials do offer full porosity (e.g. the replamineform process for hydroxyapatite), they have properties inferior to metals as discussed previously. The open cell metal structure is osteoconductive, like other porous implants. Also, it is entirely biocompatible, based on the demonstrated biocompatibility of select metals such as tantalum.

Allowing full mineralization is another property of implantable bone substitute materials. The highly-organized process of bone formation is a complex process. There are certain prerequisites for mineralization such as adequate pore size, (e.g., larger than 150 μm) with interconnect size in the range of from about 50 μm to about 100 μm, about 70 μm to about 80 μm, or less than, equal to, or greater than about 50 μm, 55, 60, 65, 70, 75, 80, 85, 90, 95, or about 100 μm. A pore diameter of about 150 μm to about 250 μm, about 190 μm to about 210 μm, or less than, equal to, or greater than about 150 μm, 160, 170, 180, 190, 200, 210, 220, 230, 240, or 250 μm corresponds to the average diameter of an osteon in human bone, while a pore diameter of from about 400 μm to about 600 μm, 490 μm to about 510 μm, or less than, equal to, or greater than about 400 μm, 410, 420, 430, 440, 450, 460, 470, 480, 490, 500, 510, 520, 530, 540, 550, 560, 570, 580, 590, or about 600 μm corresponds to remodeled cancellous bone. The implantable structures of the present invention can be fabricated to virtually any desired porosity and pore size, and can thus be matched perfectly with the surrounding natural bone in order to provide an optimal matrix for ingrowth and mineralization. Such close matching and flexibility are generally not available with other porous implant materials.

One consideration with an implantable material must be the potential for stress shielding. According to Wolff's law, bone grows where it is needed (that is, where there is a stress). Stress on a bone normally stimulates that bone to grow. With an implantable material, it is primarily the stress/strain field created in the tissue around an implant that controls the interface remodeling. Stress shielding occurs when an overly stiff implant carries stresses that were previously applied to the bone in that area; it can result in inhibition of mineralization and maturation of the ingrowing bone, and/or the resorption of existing natural bone.

An implantable material, then, should distribute stresses throughout its structure, the ingrowing bone, and the surrounding bone in order to avoid bone resorption and weakening caused by stress shielding. Because metals are stronger than natural bone, this would seem to be a concern with a metallic implant in that the implant would itself focus and bear directly the majority of local loads and stresses that would ordinarily be placed on the bone, thus depriving both the existing and new bone of those forces which, in effect, help keep it at optimal density.

The unique structure and properties of the implantable material, however, may avoid this drawback. The deposited thin metallic layers operate as an array within the porous metal body, contributing their exceptional mechanical properties to the structure at large. One result of this effect is that imposed loads are distributed throughout the body. In the case of an open cell metal bone implant, stresses are distributed into both the ingrowing new bone and the surrounding existing bone as well, thereby providing both the old and new bone with the normal, healthy forces they require.

In fact, with the ability to finely tailor the open cell metal structure's properties during the fabrication process, the implantable material can be designed to distribute stresses in a given direction(s), depending on the needs of the specific application at hand. The bonding of regenerated bone to the implant also helps to transfer stresses directly to the bone in and around the implant; this sharing of biofunction is a consequence of the composite nature of the implant/bone structure. An advantage of these metal structures over other porous implant materials is especially strong in this area. Ceramics lack sufficient mechanical properties to begin with, and no current implant material, either ceramic or metallic, possesses the unique properties of the metal structure as described here.

Figure 2:
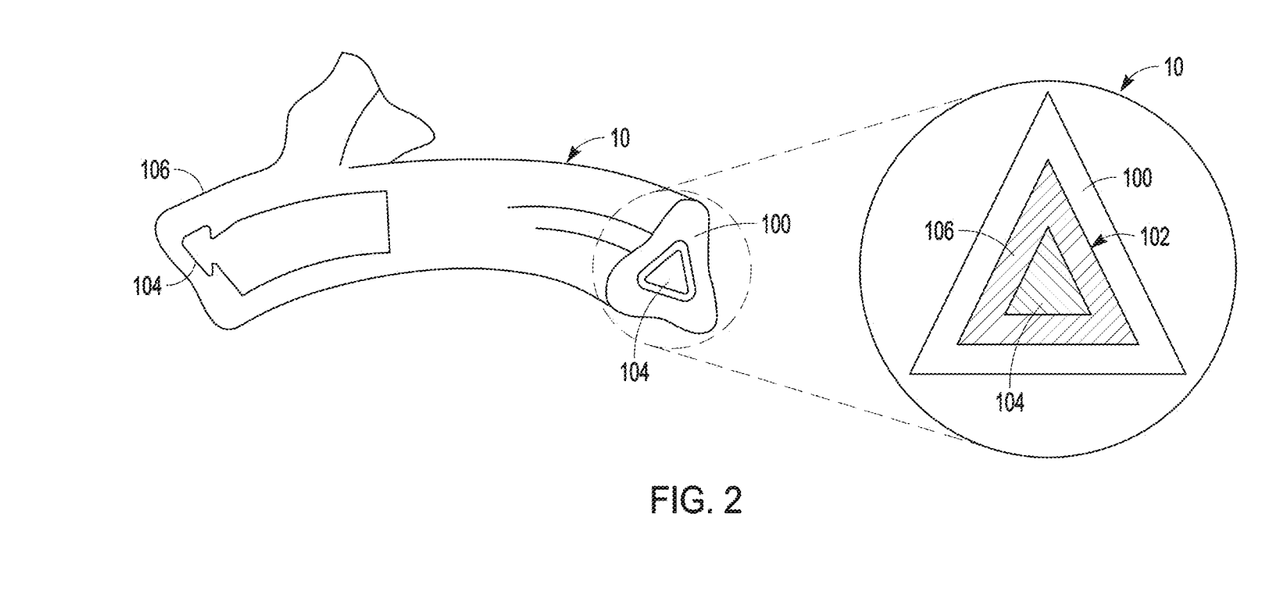
FIG. 2 is an image of a section of the implantable material showing ligamental structure and an individual coated ligament in cross-section, according to various embodiments.

Implantable material 10 exhibits many of the desired properties described herein. Implantable material 10 may be included in an implant for use as a cancellous bone substitute or a cell and tissue reception material. An example of implantable material 10 is shown as a perspective view in FIG. 1. As shown in FIG. 1, implantable material 10 includes open spaces 100 interconnected by ligaments 102. With the variables available in both the materials and the fabrication process, it is possible to obtain the simultaneous optimization of multiple properties (e.g. strength, stiffness, density, weight) for the given application of substitution for bone. FIG. 2 is a sectional view of implantable material 10 showing the ligamental structure and an individual coated ligament in cross-section, respectively. In FIG. 2 it can be seen that each ligament 102 is formed by substrate 104 covered by thin monolithic layer 106 of a biocompatible metal. The term monolithic means that the layer is a single layer. Open spaces 100, between the ligaments, form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

Substrate 104 can be any suitable substrate material. Examples of suitable materials include a reticulated open cell substrate and a solid densified substrate. Reticulated open cell substrates may include a lightweight substantially rigid foam carbonaceous material. The carbonaceous material may include open spaces defining an interconnecting network. The carbonaceous material may include any suitable material such as carbon, graphite, and a mixture thereof. Alternatively, the reticulated open cell substrate may include a lightweight substantially rigid foam ceramic material or titanium. The ceramic material or titanium may include open spaces defining an interconnecting network. The ceramic can include a refractory ceramic material. Solid densified substrates may include a metal such as titanium or an alloy thereof.

Substrate 104 can have a surface of any suitable shape. The surface can be substantially planar. The surface can further constitute an undulating surface. In other examples, the surface can have a generally curved profile. Substrate 104 can be formed through many suitable techniques. For example, substrate 104 can be formed through die casting, injection molding, or additive manufacturing.

Monolithic layer of a biocompatible metallic material 106 is deposited on substrate 104. As described further herein, monolithic layer 106 is not deposited through a chemical-vapor-deposition (CVD) technique. As a result, monolithic layer 106 has at least one of an amorphous and a crystalline microstructure, understood to refer to the structure of a material as revealed by a microscope above 25× magnification. The amorphous or crystalline microstructure can independently range from about 0 wt % to about 100 wt % of monolithic layer 106, about 25 wt % to about 75 wt %, or less than, equal to, or greater than about 0 wt %, 5, 10, 15, 20, 25, 30, 35, 40, 45, 50, 55, 60, 65, 70, 75, 80, 85, 90, 95, or about 100 wt %. The biocompatible metal can be any metal that is suitable for integration with a biological system. Some factors that may determine whether a metal is compatible include the toxicity of the metal or whether the metal will provoke an allergic reaction in the biological system. Examples of suitable biocompatible metals include tantalum, niobium, titanium, silver, gold, platinum, copper, silver-gold-platinum alloy, cobalt-chrome alloy, an alloy thereof, or a mixture thereof. An example a suitable structure is produced using Trabecular Metal™ Technology available from Zimmer, Inc., of Warsaw, Ind. Trabecular Metal™ is a trademark of Zimmer, Inc.

As shown in FIGS. 1 and 2, monolithic layer or film 106 is disposed over 100% of the surface area of substrate 104. In other examples, monolithic layer 106 can be disposed over a range of from about 60% to about 100% surface area of substrate 104, or less than, equal to, or greater than about 60%, 65, 70, 75, 80, 85, 90, 95, or 100% surface area of substrate 104. As an example, the thickness of monolithic layer 106 may be in a range of from about 1 micron to about 75 microns, about 5 microns to about 60 microns, or less than, equal to, or greater than about 1 micron, 5, 10, 15, 20, 25, 30, 35, 40, 45, 50, 55, 60, 65, 70, or 75 microns. The thickness of monolithic layer 104 can be constant or variable.

Implantable material 10 can include a second layer or layer of the biocompatible metallic material deposited on monolithic layer 106. The second layer can include the same biocompatible metallic material or a different biocompatible metallic material as compared to that of monolithic layer 106. The second layer can be deposited on monolithic layer 106 through a CVD process. The second layer can be disposed over a range of from about 60% to about 100% of the surface area of monolithic layer 106, or less than, equal to, or greater than about 60%, 65, 70, 75, 80, 85, 90, 95, or 100% of the surface area of monolithic layer 106. The second layer can have a constant or variable thickness. Alternatively, the second layer can be a second monolithic layer of the biocompatible metallic material.

When monolithic layer 106 and the second layer are joined, they can together form a biocompatible metallic layer. Relative to each other, a maximum thickness of monolithic layer 106 is greater than a maximum thickness of the second layer. For example, monolithic layer 106 may range from about 2 times to about 50 times thicker than the second layer, about 5 times to about 20 times, or less than, equal to, or greater than about 2 times, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times thicker than the second layer. Monolithic layer 106 accounts for a greater wt % of the metallic layer. For example, monolithic layer 106 can range from 60 wt % to about 99 wt % of the biocompatible metallic layer, about 85 wt % to about 95 wt %, or less than, equal to, or greater than about 60 wt %, 65, 70, 75, 80, 85, 90, 95, or 99 wt % of the biocompatible metallic layer.

The implantable material is formed according to a method that can be free of a CVD process. According to various examples, the method can include contacting the substrate with a gaseous or molten liquid monolithic layer precursor. Upon contact, at least a portion of the monolithic layer precursor is reduced on the substrate to form the monolithic layer of the biocompatible material.

In embodiments, where the monolithic layer precursor is gaseous or liquid, the method can be carried out in closed (e.g., sealed) environment. The environment can be free of oxygen or any other component.

The gaseous or liquid monolithic layer precursor can be a halogenated biocompatible metallic material that can include a non-elemental halogenated compound of any of the biocompatible metallic materials described herein. In examples where the biocompatible metallic material of the monolithic layer is tantalum, examples of suitable halogenated compounds tantalum fluoride, tantalum bromide, tantalum chloride, tantalum iodide, and a mixture thereof. An example of a tantalum chloride is tantalum pentachloride. An example of a tantalum fluoride is potassium tantalum fluoride.

The monolithic layer precursor can be provided in the environment, in a gaseous state or brought to a gaseous state therein. The precursor can be brought to a gaseous state though sublimation (e.g., solid state directly to gaseous state) or through vaporization (e.g., solid state, to liquid state, to gaseous state or liquid state to gaseous state). If the monolithic layer precursor is liquid, the solid counterpart can be heated to a molten state and the substrate can be contacted with the liquid. The substrate can be rotated or agitated in the liquid or gaseous monolithic layer precursor to enhance coverage.

The temperature and pressure in the environment can be optimized to facilitate contact between substrate 104 and the precursor. For example, a temperature in the environment can be in a range of from about 200° C. to about 600° C., about 350° C. to about 450° C., or less than, equal to, or greater than about 200° C., 250, 300, 350, 400, 450, 500, 550, or 600° C. A pressure can be less than about 1 ATM, less than about 0.5 ATM, less than 0.1 ATM or less than 0.01 ATM. To help increase the distribution or uniformity of the precursor on substrate 104, substrate 104 can be rotated or shaken within the environment as the precursor is deposited thereon.

Following deposition, halogenated precursor is reduced in situ to its elemental form on substrate 104. Reduction can be accomplished by contacting the precursor with a reducing agent. The reducing agent can be chosen from many suitable reducing agents. Examples of suitable reducing agents include gaseous hydrogen, sodium hydride, sodium borohydride, or a combination thereof. In examples where the reducing agent is hydrogen gas, the hydrogen can be supplied to the environment by a plasma jet. To enhance the reduction of the precursor the temperature and the pressure in the environment can be tuned. In some examples, during reduction, a temperature of the environment can be a range of from about 25° C. to about 900° C., about 25° C. to about 600° C., or less than, equal to, or greater than about 25° C., 50, 100, 150, 200, 250, 300, 350, 400, 450, 500, 550, 600, 650, 700, 750, 800, 850, or about 900° C. A pressure within the environment can be is performed at a pressure of less than about 0.1 ATM, or less than about 0.5 ATM, or less than about 0.1 ATM.

Following reduction of the precursor to form monolithic layer 106, a second layer can be optionally deposited thereon through CVD. In the CVD process an elemental metal may be halogenated in a halogenation chamber. The halogenated metal can then be reduced to an elemental form and deposited on monolithic layer 106.

Following the contacting and deposition steps, implantable material 10 may be subjected to any number of post-processing steps. For example, in order to reduce the porosity of material 10, material 10 may be densified. Densification can occur, for example, by heating material 10. Through densification, the material 10, or individual layers thereof, can be brought to 20% to 100% of an ideal density (e.g., 100% density with 0% porosity), 40% to 70%, or less than, equal to, or greater than about 20%, 25, 30, 35, 40, 45, 50, 55, 60, 65, 70, 75, 80, 85, 90, 95, or 100% of an ideal density of material 10. The density can be selected in order to tailor the structure for particular orthopedic applications, for example, by matching the structure to surrounding natural tissue in order to provide an improved matrix for tissue ingrowth and mineralization. Such structures can be isotropic or anisotropic. In this regard, according to certain embodiments, an open porous metal structure may be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure may have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

The structural integrity of implantable structure 10 is provided by the deposited biocompatible metallic layers themselves, rather than by substrate 104. These metallic layers have much higher moduli of elasticity than do the thin sections of, for example, vitreous carbon in substrate 104.

Through the method described herein, implantable structure is readily shapeable to nearly any configuration, simple or complex, simply by shaping substrate 104 prior to biocompatible metal deposition. This facilitates exact contouring of implant 10 for the specific application and location; precise placement is enhanced and bulk displacement is prevented. Additionally, any final shaping/trimming needed at surgery can be accomplished on the final material 10 using conventional dental or orthopedic equipment available at the time of surgery.

The optimal conditions for fracture healing and long-term stability can be met if an implant can be designed allowing for motionlessness along all the interfaces necessary for a stable anchorage, thereby excluding (to the greatest extent possible) all outside influences on the remodeling process and allowing the local stress/strain field to control.

Following implantation and initial tissue ingrowth, the implantable device 10 can stay where it is placed without retention aids, a reflection of precise contouring and the rapid ingrowth of fibrovascular tissue to prevent dislodgement. The binding between bone and implant 10 stabilizes the implant and prevents loosening. These implants thus will not need to be held in place by other means (e.g. sutures or cement); rather, the growth of a natural bone-to-porous structure seal is encouraged by the nature of the implant itself. Tissue ingrowth would not be a contributing factor to device retention for a period following implantation, however, until a substantial amount of ingrowth had occurred.

The ability to precisely contour the device, along with its surface texture that provides multipoint contact with the surrounding tissue, is of some aid in retention, although mechanical aids may still be necessary at first.

EXAMPLES

Various embodiments of the present disclosure can be better understood by reference to the following Examples, which are offered by way of illustration. The present disclosure is not limited to the Examples given herein.

An implant including a monolithic layer of a biocompatible metallic material was created generally, following two steps. Those two steps include: (1) deposition of the tantalum metal precursor to a substrate followed by (2) conversion of the precursor to the biocompatible metallic material.

The substrate was a reticulated vitreous carbon (RVC). RVC is an open pore vitreous carbon foam. The tantalum metal precursor was disposed as a vapor comprised mainly of an argon carrier with a low concentration of the tantalum metal precursor. This gas stream was passed through a set of RVC plugs, held at a lower temperature than the gas stream, to condense the tantalum metal precursor evenly throughout the RVC structures.

Figure 3:
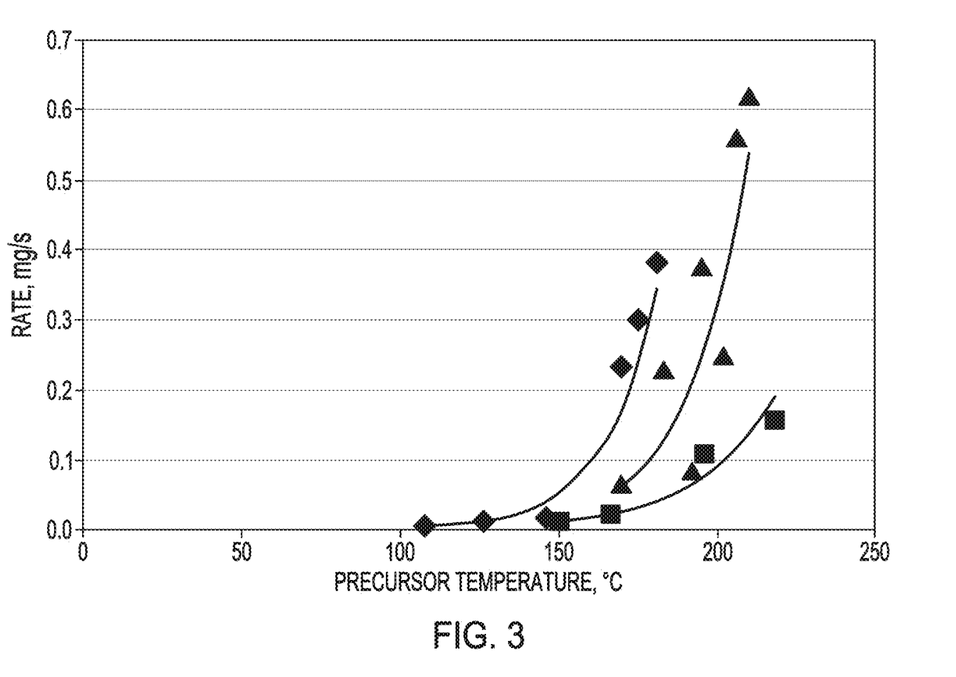
FIG. 3 is a graph showing the amount of tantalum pentachloride deposited on a pipette, according to various embodiments.

The tantalum precursor included tantalum pentachloride ($TaCl_5$) Tantalum pentachloride produced a significant vapor phase concentration at temperatures below its melting point of 218° C. When the tantalum pentachloride, in a powder form, was heated to a temperature between 180-200° C., with an argon flow over the powder (~50 sccm), a pre-weighed, room temperature (24±2° C.) Pasteur pipette was inserted into the outlet of a graphite lid of a closed assembly, for a timed period which ranged from about 1-5 minutes. This lead to condensation of the tantalum pentachloride on the walls of the pipette. The pipette was then removed and weighed. The results of these experiments confirmed a satisfactory rate of $TaCl_5$ mass would be transported out of sublimation and deposited on the pipette in this temperature range. The results of three studies (indicated with diamond, triangular, and square data points, respectively) are shown in FIG. 3. To study the ability to deposit tantalum pentachloride on an RVC substrate the pipette was replaced with an RVC plug with this precursor.

To test the ability to deposit on an RVC substrate, a glass tube (12.0 mm inner diameter×136 mm length), was wrapped with 20 turns of 20 gauge wire which served as a heating coil. At five locations, equi-spaced along the tube, K-type thermocouples were attached. Four pre-weighed RVC plugs (12.0 mm inner diameter×15.0 mm length cylinders) were press fit into the tube. The entire assembly was then wrapped with a 3 mm thick Aramid thermal fabric. The assembly was fit into a groove in lid of a sealed container through which the tantalum pentachloride laden argon gas stream was fed. Tantalum pentachloride, in a 150 mL beaker, was heated to 190±2° C. under an argon gas stream (50 sccm) to produce the precursor vapor stream. The lid was kept at 200-210° C. to prevent condensation of tantalum pentachloride. The thermocouple was used with a digital temperature controller to power the heating coil and maintain a temperature of 180±2° C. at the midpoint position. During the coating, the plugs were exposed to 30 min of the tantalum pentachloride laden argon stream and then the system cooled. When cool, the glass tube was removed and the now coated plugs removed by forcing a steel rod (a ramrod) through the tube.

Figure 4:
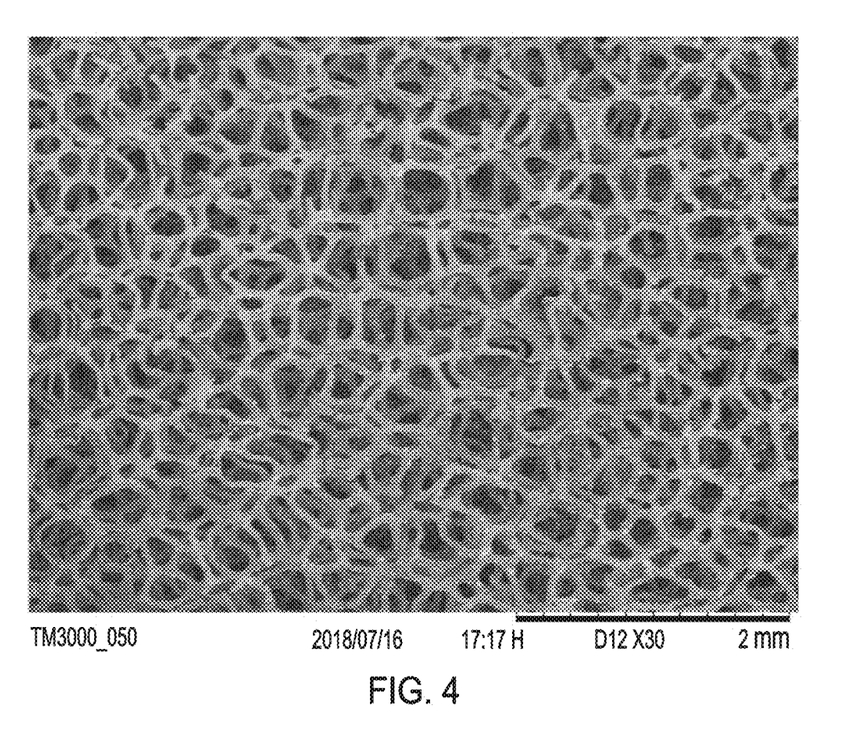
FIG. 4 is a micrograph taken at a magnification at 30× of an RVC plug, according to various embodiments.
Figure 5:
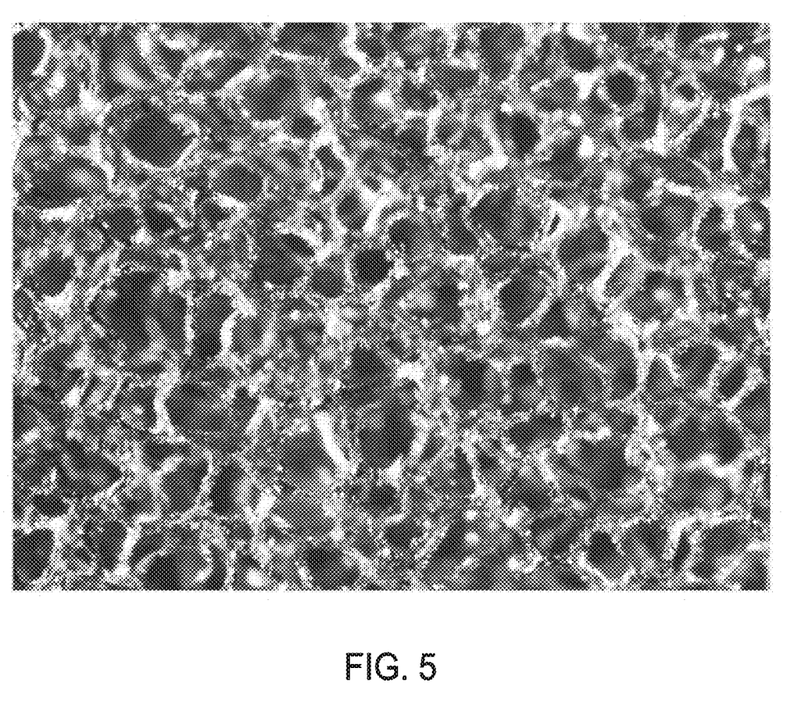
FIG. 5 is micrograph taken at a magnification at 30× of another RVC plug covered in tantalum, according to various embodiments.

The coated plugs were cut lengthwise and imaged. Plugs from two trials were examined at 30× magnifications. Examination showed that there was one plug from each trial showing a uniform coating of the RVC network. Images of these plugs are shown in FIG. 4 (an SEM image) and 5 (an optical microscope image). These images show the uniformity of the tantalum pentachloride layer. The uniformly coated plugs came from a region of the tube corresponding to a temperature of about 180° C.

This example showed that it was possible to uniformly coat the inside, as well as the outside, of RVC plugs with a tantalum precursor, such as tantalum pentachloride.

The tantalum precursor can also be reduced to metal, by exposing the tantalum precursor in a gaseous phase to hydrogen plasma at a low temperature. The temperature can be as low as room temperature with an upper temperature being any value just below the melting point of the tantalum precursor at the specific pressure to which the tantalum precursor is exposed. For example, when the tantalum precursor was tantalum pentachloride and the pressure in the system was 0.0021 ATM, the upper temperature to which the tantalum precursor could be exposed was 115° C. With this, the tantalum precursor is reduced to tantalum metal, in place within the RVC structure.

To carry out this experiment, the RVC workpiece exposed to gaseous tantalum pentachloride inside a hermetically sealed chamber. The pressure inside the chamber was reduced to 0.0021 ATM. Hydrogen gas was supplied to the chamber and microwave radiation having a frequency of 2.45 GHz was supplied to the chamber to generate a hydrogen plasma, which reduced the gaseous tantalum pentachloride to tantalum metal on the RVC plug. The temperature did not exceed 115° C. The results showed that it was possible to uniformly coat the inside, as well as the outside, of RVC plugs with a gaseous tantalum precursor, such as tantalum pentachloride using hydrogen plasma.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

ADDITIONAL EMBODIMENTS

The following exemplary embodiments are provided, the numbering of which is not to be construed as designating levels of importance:

Embodiment 1 provides an implant comprising:
a substrate; and
a monolithic layer comprising a biocompatible metallic material, having at least one of an amorphous and a crystalline microstructure contacting the substrate.

Embodiment 2 provides the implant of Embodiment 1, wherein the implant is a cancellous bone substitute or a cell and tissue reception material.

Embodiment 3 provides the implant of Embodiment any one of Embodiments 1 or 2, wherein the substrate is chosen from at least one of a reticulated open cell substrate and a solid densified substrate.

Embodiment 4 provides the implant of Embodiment 3, wherein the reticulated open cell substrate comprises a lightweight substantially rigid foam carbonaceous material having open spaces comprising an interconnecting network.

Embodiment 5 provides the implant of Embodiment 4, wherein the carbonaceous material is chosen from carbon, graphite, and a mixture thereof.

Embodiment 6 provides the implant of Embodiment 3, wherein the reticulated open cell substrate comprises a lightweight substantially rigid foam ceramic material or titanium having open spaces comprising an interconnecting network.

Embodiment 7 provides the implant of Embodiment 6, wherein the ceramic is a refractory.

Embodiment 8 provides the implant of Embodiment 3, wherein the solid densified substrate comprises a metal.

Embodiment 9 provides the implant of any one of Embodiments 1-8, wherein the substrate comprises an undulating surface.

Embodiment 10 provides the implant of Embodiment 8, wherein the metal is titanium or open cell titanium.

Embodiment 11 provides the implant of any one of Embodiments 1-10, wherein the biocompatible metallic material comprises titanium, niobium, silver, gold, platinum, copper, silver-gold-platinum alloy, cobalt-chrome alloy, an alloy thereof, or a mixture thereof.

Embodiment 12 provides the implant of any one of Embodiments 1-11, wherein the biocompatible metallic material comprises tantalum.

Embodiment 13 provides the implant of any one of Embodiments 1-12, wherein the monolithic layer is disposed over about 90% surface area to about 100% surface area of the substrate.

Embodiment 14 provides the implant of any one of Embodiments 1-13, wherein the monolithic layer is disposed over about 95% surface area to about 100% surface area of the substrate.

Embodiment 15 provides the implant of any one of Embodiments 1-14, wherein the monolithic layer has a constant thickness.

Embodiment 16 provides the implant of any one of Embodiments 1-15, wherein the monolithic layer has a variable thickness.

Embodiment 17 provides the implant of any one of Embodiments 1-16 and further comprising a second layer of a second biocompatible material contacting the monolithic layer.

Embodiment 18 provides the implant of Embodiment 17, wherein the second layer is deposited by chemical-vapor deposition.

Embodiment 19 provides the implant of any one of Embodiments 17 or 18, wherein the biocompatible metallic material comprises titanium, tantalum, niobium, silver, gold, platinum, copper, silver-gold-platinum alloy, cobalt-chrome alloy, an alloy thereof, or a mixture thereof.

Embodiment 20 provides the implant of any one of Embodiments 17-19, wherein the biocompatible metallic material comprises tantalum.

Embodiment 21 provides the implant of any one of Embodiments 17-20, wherein the second layer is disposed over about 90% surface area to about 100% surface area of the monolithic layer.

Embodiment 22 provides the implant of any one of Embodiments 17-21, wherein the second layer is disposed over about 95% surface area to about 100% surface area of the monolithic layer.

Embodiment 23 provides the implant of any one of Embodiments 17-22, wherein the second layer has a constant thickness.

Embodiment 24 provides the implant of any one of Embodiments 17-23, wherein the second layer has a variable thickness.

Embodiment 25 provides the implant of any one of Embodiments 17-24, wherein a maximum thickness of the monolithic layer is greater than a maximum thickness of the second layer.

Embodiment 26 provides the implant of any one of Embodiments 17-25, wherein the monolithic layer and the second layer are joined to form a biocompatible metallic layer.

Embodiment 27 provides the implant of Embodiment 26, wherein the monolithic layer comprises about 60 wt % to about 99 wt % of the biocompatible metallic layer.

Embodiment 28 provides the implant of Embodiment 26, wherein the monolithic layer comprises about 85 wt % to about 95 wt % of the biocompatible metallic layer.

Embodiment 29 provides a method of making the implant of any one of Embodiments 1-28, the method comprising:
contacting the substrate with a monolithic layer precursor; and
reducing at least a portion of the monolithic layer precursor on the substrate to form the monolithic layer of the biocompatible material.

Embodiment 30 provides the method of Embodiment 29, wherein the monolithic layer precursor comprises a halogenated biocompatible metallic material.

Embodiment 31 provides the method of any one of Embodiment 29 or 30, wherein the monolithic layer precursor comprises tantalum fluoride, tantalum bromide, tantalum chloride, tantalum iodide, or a mixture thereof.

Embodiment 32 provides the method of any one of Embodiments 29-31, wherein the monolithic layer precursor comprises tantalum chloride, potassium tantalum fluoride, or a mixture thereof.

Embodiment 33 provides the method of any one of Embodiments 29-32, further comprising at least one of subliming and vaporizing the monolithic layer precursor.

Embodiment 34 provides the method of any one of Embodiments 29-33, further comprising contacting the monolithic layer precursor with a reducing agent to reduce the precursor.

Embodiment 35 provides the method of Embodiment 34, wherein the reducing agent is chosen from hydrogen, sodium hydride, sodium borohydride, or a combination thereof.

Embodiment 36 provides the method of Embodiment 35, wherein the hydrogen gas is supplied by a plasma jet.

Embodiment 37 provides the method of any one of Embodiments 29-36, wherein the method is performed in a closed environment.

Embodiment 38 provides the method of Embodiment 37, wherein contacting the substrate with the gaseous monolithic layer precursor is performed at a temperature in a range of from about 200° C. to about 600° C.

Embodiment 39 provides the method of any one of Embodiments 37 or 38, wherein contacting the substrate with the gaseous monolithic layer precursor is performed at a temperature in a range of from about 350° C. to about 450° C.

Embodiment 40 provides the method of any one of Embodiments 37-39, wherein the contacting the substrate with the gaseous monolithic layer precursor is performed at a pressure in a range of less than about 1 ATM.

Embodiment 41 provides the method of any one of Embodiments 37-40, wherein reducing the gaseous monolithic layer precursor is performed at a temperature in a range of from about 25° C. to about 900° C.

Embodiment 42 provides the method of any one of Embodiments 37-41, wherein reducing the gaseous monolithic layer precursor is performed at a temperature in a range of from about 25° C. to about 600° C.

Embodiment 43 provides the method of any one of Embodiments 37-42, wherein reducing the gaseous monolithic layer precursor is performed at a pressure of less than about 0.1 ATM.

Embodiment 44 provides the method of any one of Embodiments 29-43, further comprising depositing the second layer of the biocompatible material on the first layer of the biocompatible material by chemical-vapor deposition.

Embodiment 45 provides the method of any one of Embodiments 29-44, further comprising heating at least one of the first layer and the second layer to densify the at least one first layer and second layer.

Embodiment 46 provides the method of Embodiment 45, wherein at least one of the first and second layer are densified to 20% to 100% of an ideal density.

Embodiment 47 provides the method of any one of Embodiments 29-46, wherein the gaseous monolithic layer precursor is uniformly distributed about a surface area of the substrate.

What is claimed is:

1. An implant comprising:
   a substrate comprising a reticulated open cell substrate comprising a lightweight substantially rigid foam carbonaceous material;
   a monolithic layer comprising a biocompatible metallic material, the biocompatible metallic material comprising at least one of an amorphous and a crystalline microstructure contacting the substrate, wherein the monolithic layer is deposited according to a process that is not chemical-vapor deposition; and
   a second layer comprising a second biocompatible metallic material joined to the monolithic layer, wherein the second layer is deposited by chemical-vapor deposition,
   wherein a thickness of the monolithic layer is in a range of from about 1 micron to about 75 microns and is in a range of from 5 times to 50 times greater than a thickness of the second layer.

2. The implant of claim 1, wherein the reticulated open cell substrate comprising a lightweight substantially rigid foam carbonaceous material comprises open spaces comprising an interconnecting network.

3. The implant of claim 1, wherein the carbonaceous material is chosen from carbon, graphite, and a mixture thereof.

4. The implant of claim 1, wherein the substrate comprises an undulating surface.

5. The implant of claim 1, wherein the biocompatible metallic material comprises titanium, tantalum, niobium, silver, gold, platinum, copper, silver-gold-platinum alloy, cobalt-chrome alloy, an alloy thereof or a mixture thereof.

6. The implant of claim 1, wherein the biocompatible metallic material comprises tantalum, titanium, alloys thereof or a mixture thereof.

7. The implant of claim 1, wherein the second biocompatible metallic material contacting the monolithic layer comprises tantalum, titanium, an alloy thereof, or a mixture thereof.

8. The implant of claim 1, wherein the thickness of the monolithic layer is in a range of from 5 times to 20 times greater than a thickness of the second layer.

9. A method of making the implant of claim 1, the method comprising:
   contacting the substrate with a monolithic layer precursor comprising a biocompatible metallic material; and
   reducing at least a portion of the monolithic layer precursor on the substrate to form the monolithic layer of the biocompatible material having at least one of an amorphous and a crystalline microstructure.

10. The method of claim 9, wherein the monolithic layer precursor comprises a halogenated biocompatible metallic material.

11. The method of claim 9, wherein the monolithic layer precursor comprises tantalum fluoride, tantalum bromide, tantalum chloride, tantalum iodide, or a mixture thereof.

12. The method of claim 9, wherein the monolithic layer precursor is tantalum pentachloride, potassium tantalum fluoride, or a mixture thereof.

13. The method of claim 9, wherein the monolithic layer precursor is in a gaseous phase or a liquid phase.

14. The method of claim 9, further comprising at least one of subliming the monolithic layer precursor and vaporizing the monolithic layer precursor.

15. The method of claim 9, further comprising contacting the monolithic layer precursor with a reducing agent to reduce the precursor.

16. The method of claim 15, wherein the reducing agent is chosen from hydrogen, sodium hydride, sodium borohydride, or a combination thereof.

17. The method of claim 9, wherein contacting the substrate with the gaseous monolithic layer precursor is performed at a temperature in a range of from about 200° C. to about 600° C.

18. The method of claim 9, wherein contacting the substrate with the gaseous monolithic layer precursor is performed at a pressure in a range of less than about 1 ATM.

19. The method of claim 9, further comprising depositing the second layer of the biocompatible material on the first layer of the biocompatible material by chemical-vapor deposition.

20. The implant of claim 1, wherein the monolithic layer comprising a biocompatible metallic material comprises an amorphous microstructure.

* * * * *

UNITED STATES PATENT AND TRADEMARK OFFICE
CERTIFICATE OF CORRECTION

PATENT NO. : 11,419,725 B2
APPLICATION NO. : 16/194729
DATED : August 23, 2022
INVENTOR(S) : Zitelli et al.

It is certified that error appears in the above-identified patent and that said Letters Patent is hereby corrected as shown below:

In the Claims

In Column 14, Line 22, in Claim 5, delete "thereof or", insert --thereof, or-- therefor In Column 14, Line 25, in Claim 6, delete "thereof or", insert --thereof, or-- therefor Signed and Sealed this
Sixteenth Day of July, 2024

Katherine Kelly Vidal
*Director of the United States Patent and Trademark Office*